US008980621B2

(12) United States Patent
Kopp

(10) Patent No.: US 8,980,621 B2
(45) Date of Patent: Mar. 17, 2015

(54) HIGH-DENSITY MULTIWELL-PLATE

(75) Inventor: Martin Kopp, Huenenberg See (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 1408 days.

(21) Appl. No.: 12/546,940

(22) Filed: Aug. 25, 2009

(65) Prior Publication Data

US 2010/0055770 A1 Mar. 4, 2010

(30) Foreign Application Priority Data

Aug. 26, 2008 (EP) .................................... 08015011

(51) Int. Cl.
*C12M 3/00* (2006.01)
*B01L 3/00* (2006.01)

(52) U.S. Cl.
CPC ......... *B01L 3/50851* (2013.01); *B01L 3/50853* (2013.01); *B01L 2200/142* (2013.01); *B01L 2300/0829* (2013.01); *B01L 2300/0854* (2013.01)
USPC ........................................................ 435/287.2

(58) Field of Classification Search
CPC ............ B01L 3/50851; B01L 3/50853; B01L 2300/0829; B01L 2300/0854
USPC ................................ 435/287.2, 288.5, 305.2
See application file for complete search history.

(56) References Cited

U.S. PATENT DOCUMENTS

| | | | | |
|---|---|---|---|---|
| 5,948,673 | A * | 9/1999 | Cottingham | 435/287.2 |
| 5,972,694 | A * | 10/1999 | Mathus | 435/288.4 |
| 2002/0025280 | A1 | 2/2002 | Chazan et al. | |
| 2003/0032076 | A1 * | 2/2003 | Duffy et al. | 435/7.92 |
| 2004/0067171 | A1 * | 4/2004 | Icke et al. | 422/102 |
| 2007/0003443 | A1 * | 1/2007 | Sandell et al. | 422/100 |
| 2008/0247916 | A1 | 10/2008 | Inaba et al. | |
| 2009/0170183 | A1 | 7/2009 | Buchs | |

FOREIGN PATENT DOCUMENTS

| | | | |
|---|---|---|---|
| DE | 10 2006 025 011 | A1 | 11/2007 |
| GB | 2 369 086 | A | 5/2002 |
| WO | 00/69560 | A1 | 11/2000 |
| WO | 00/78455 | A1 | 12/2000 |
| WO | 03/061832 | A1 | 7/2003 |
| WO | 2005/028109 | A2 | 3/2005 |

OTHER PUBLICATIONS

European Search Report, Feb. 19, 2009 for Application No./Patent No. 08015011.3-2113, pp. 1-5.

* cited by examiner

*Primary Examiner* — Jonathan Hurst
(74) *Attorney, Agent, or Firm* — Denise M. Everett

(57) ABSTRACT

A high-density multiwell-plate for performing thermocycled amplification reactions of polynucleotides in liquid samples comprising a plurality of reaction wells is disclosed. In order to provide a better thermal insulation, the plate comprises a rigid well-forming structure placed above a bottom layer, wherein substantially horizontal well-covering areas cover the liquid sample comprised in the wells, and a substantially plane cover placed above the well-forming structure providing a thermal insulating air distance between the well-covering areas and the cover.

20 Claims, 10 Drawing Sheets

HIGH-DENSITY MULTIWELL-PLATE

INVENTIVE FIELD

Embodiments of the present invention relate generally to multiwell-plates used for analyzing samples, and particular to a high-density multiwell-plate for performing thermocycled amplification reactions of polynucleotides in liquid samples.

BACKGROUND

Multiwell-plates are used for analyzing samples typically with a nucleic acid amplification technique. The purpose of the analysis is the detection (presence or absence of an analyte) and/or the quantification of the concentration of an analyte in samples. In the current invention the analyte is a nucleic acid: RNA or DNA or derivatives there off. The derivatives (Nucleic Acids, NA) mentioned include molecules which are accessible directly or indirectly (e.g. after chemical modification) to a NA amplification method (e.g. DNA-polymerase, Transcriptase, Reverse-Transcriptase, etc.). The target analytes can be e.g. genetic material with biological origin e.g. for genetic testing, in case of infectious diseases the analyte can be nucleic acid material from a virus or bacteria, in case of gene-expression the analytes can be m-RNAs, the analyte can also be methylated DNA.

A variety of tools and techniques have been developed to detect and investigate the structure and function of individual genes and the proteins they express. Such tools include polynucleotide probes, which comprise relatively short, defined sequences of nucleic acids, typically labeled with a radioactive or fluorescent moiety to facilitate detection. Probes may be used in a variety of ways to detect the presence of a polynucleotide sequence, to which the probe binds, in a mixture of genetic material. Nucleic acid sequence analysis is also an important tool in investigating the function of individual genes. Several methods for replicating, or “amplifying,” polynucleic acids are known in the art, notably including polymerase chain reaction (PCR). Indeed, PCR has become a major research tool, with applications including cloning, analysis of genetic expression, DNA sequencing, and genetic mapping.

There are many circumstances in which multiple batch reactions need to be performed such as Genotyping applications. DNA amplifications by means of polymerase chain reaction (PCR) or primer extension is a method routinely used in genotyping, such as SNP (single nucleotide polymorphism) analysis. SNP specific targets are observed via reaction plate from either top or bottom (after a PCR amplification, primer extension or hybridization step) or sample/reagent removed and interpreted via spectroscopy, mass spectroscopy, sequencing or hybridization. These batch reactions can be performed on reaction plates. These reaction plates, in many such applications, are often referred to as microtitre plates. These reaction plates have generally supplied as injection molded, one piece reaction plates having multiple wells formed therein in the form of miniature test tubes.

In general, the purpose of a polymerase chain reaction is to manufacture a large volume of DNA that is identical to an initially supplied small volume of “target” or “seed” DNA. The reaction involves copying the strands of the DNA and then using the copies to generate other copies in subsequent cycles. Each cycle will double the amount of DNA present thereby resulting in an exponential progression in the volume of copies of the target DNA strands present in the reaction mixture. In general, the purpose of PCR is to manufacture a large quantity of DNA which is identical to an initially supplied small quantity of target or seed DNA. The reaction involves copying the strands of the DNA and then using the copies to generate other copies in subsequent cycles.

A typical PCR temperature cycle requires that the reaction mixture be held accurately at each incubation temperature for a prescribed time and that the identical cycle or a similar cycle be repeated many times. For example, a PCR program may start at a sample temperature of 94° C. held for 30 seconds to denature the reaction mixture. Then, the temperature of the reaction mixture is lowered to 37° C. and held for one minute to permit primer hybridization. Next, the temperature of the reaction mixture is raised to a temperature in the range from 50° C. to 72° C. where it is held for two minutes to promote the synthesis of extension products. This completes one cycle. The next PCR cycle then starts by raising the temperature of the reaction mixture to 94° C. again for strand separation of the extension products formed in the previous cycle (denaturation). Typically, the cycle may be repeated 20 to 30 times.

During a typical PCR process, a small quantity of the sample and a solution of reactants, including the target, are deposited in the wells of a microtiter plate. The plate is placed in a thermocycler which operates to cycle the temperature of the contents within the wells, as described above. In particular, the microtiter plate is placed on a metal heating fixture that is shaped to closely conform to the underside of the plate and wells. A heated top plate of the thermocycler then tightly clamps the plate onto the metal heating fixture during the heating and cooling cycles.

For real time polymerase chain reaction (“PCR”) measurements, wells containing assay/sample mixtures need to be tightly sealed to prevent water evaporation during thermocycling. The thermal cycling process may include temperatures that are above the vapor point of the solutions used in the process. This creates vapor that is trapped in the wells of the microtiter plate. The presence of this vapor may cause inaccurate fluorescence or other spectrometric measurements. The trapped vapor may also contain needed reactants, thus causing incomplete reactions during the thermal cycling and may cause inaccurate measurements. Furthermore, vapor pressure may create stresses within the sample wells, causing leaking of the cover. Such leaking can lead to loss of sample and cross contamination between sample wells. Further the vapor can condense on the cover placed over the wells, thus causing both incomplete reactions due to reagents missing in the well and measurement errors in the case of optical detection. In extreme cases even the sample in a well can exsiccate.

The polymerase chain reaction (PCR) technology is a major research tool throughout molecular biology, both academically and in the pharmaceutical industry. The limitations of use of such reactions have historically been the high costs resulting from the cost of reagents (particularly the enzyme) and the relatively high volumes of reagent needed to be used in the injection molded microtitre plates; typical well volumes in prior art devices could be as large as 200 microliters. However, it could be possible to obtain effective results from plates that have smaller well volumes. To date, however, effective reaction plates of well volume down to two microliters and lower have not been readily achieved.

Another problem with the relatively large volume in the prior art devices is that the excess air gap in the wells of such reaction plates causes evaporation and condensation problems that can reduce the efficiency of the reactions. Sometimes, mineral oil will be used on top of the reaction to prevent/stop evaporation/condensation problems (oil capping). However this may give rise to problems of getting rid of the oil after the reaction has gone to completion. In the prior art it therefore has been considered to be desirable to minimize the size of the excessive air gap in the multi-well reaction plates to minimize evaporation or to avoid the need for oil capping.

Another problem of same plates according to the prior art is that the base of the prior art is complex. This makes it difficult to mate to a thermal transfer plate. Therefore, each well will not transfer externally applied heat into the wells of the reaction plate efficiently, thereby making heat dependant reactions less reliable. This results in variations in the heat transferred to the various wells in the reaction plate. It would therefore be desirable to provide a reaction plate that allows heat easily to be transferred into the wells and which transfer is uniform. Use of injection molding would appear not to allow thin enough bases to be reliably formed for such transfer to occur.

Multi-well reaction plates should have a high density of wells, i.e. a large number of wells per surface area. In conventional prior art multiwell-plates, arrays of, for example, 8 by 12 wells and 16 by 24 wells have been provided. This limits each reaction plate to 96 and 384 reactions at a time, respectively. The contemporary standard is 96 or 384 wells per plate. Also there also known reaction plates having more wells, e.g. 1,536 or 3,072, but these plates are presently not yet used in PCR because they do not fulfill the requirements described above. It would be desirable therefore to increase the number of wells at a much reduced reagent volume to allow an increased reaction turnover at reduced costs.

A further use for such reaction plates is in genotyping. Genotyping is a vast, commercial industry. Most genotyping methods require a DNA amplification process. This is also where the majority of process costs occur. By reliably and routinely working with low volumes of reagent and with high throughputs, the cost per reaction could be substantially reduced. However, prior art devices have not achieved this reliably. For this reason, costs of approximately $0.50 per reaction are frequently incurred.

The well known TaqMan™ (Applied Biosystems) biotyping systems, is a government approved systems for GMO (Genetic Modified Organisms), as well as for most large SNP clinical diagnostic markers. The existing TaqMan 7700™ system uses 8 by 12 (96) well reaction plate technology. Each well is at least approximately 200 μl in volume. By using the reaction plates of the present invention, this could be reduced to 2 μl, and less. The current TaqMan 7700™ 96 well plate will not work at these lower sample/reagent volumes due to the high internal volume problems.

The dimensions of multi-well plates are standardized, see e.g. ANSI American National Standards Institute and SBS Society for Bimolecular Sciences, Standard ANSI/SBS 2-2004. The pitch, i.e. the well-to-well step size, is usually 9 mm for plates with 96 wells, 4.5 mm for plates with 384 wells and 2.25 mm for plates with 1,536 wells.

Multi-well plates according to the prior art are described in GB 2369086 A and WO 2005/028109 A2. Further, similar reaction plates are known from the manufactures KBioscience and KBiosystems. These known plates have the common disadvantage that the bottom base of the plates is formed by a rigid plate for which a material has to be used which has a low thermal conductivity. In addition, the cover has to be heated, which is in particular a difficult task upon optical detection of the samples. However, the heating of the cover is required in order to avoid condensation of the liquid sample on the cover.

It should be noted that despite these incentives, no suitable reaction plate device, until now, had been devised.

SUMMARY

It is against the above background that a high-density multiwell-plate for performing thermocycled amplification reactions of polynucleotides in liquid samples comprising a plurality of reaction wells is disclosed. In order to provide a better thermal insulation, the plate generally comprises a rigid well-forming structure placed above a bottom layer, wherein substantially horizontal well-covering areas cover the liquid sample comprised in the wells, and a substantially plane cover placed above the well-forming structure providing a thermal insulating air distance between the well-covering areas and the cover.

In one embodiment, the plate comprises a plurality of reaction wells for thermal processing and nucleic acid amplification of the liquid samples and said plate being designed to be thermally processed by a thermal cycling means of an apparatus for analyzing the liquid samples; a substantially plane bottom layer for providing a thermal contact of the plate to a thermal cycling means; a rigid well-forming structure placed above or on the top side of the bottom layer defining single wells and providing the side walls of the wells, wherein the well-forming structure comprises rigid substantially horizontal well-covering areas that cover the liquid sample comprised in the wells at the top side of the liquid sample; and a substantially plane cover placed above or on the top side of the well-forming structure, wherein the cover provides a sealing cover of the wells and a thermal insulating air distance between the well-covering areas of the well-forming structure and the cover.

In another embodiment, a high-density multiwell-plate for performing thermocycled amplification reactions of polynucleotides in liquid samples is disclosed. The plate comprises a plurality of reaction wells for thermal processing and nucleic acid amplification of the liquid samples and said plate being designed to be thermally processed by a thermal cycling means of an apparatus for analyzing the liquid samples; a substantially plane bottom layer for providing a thermal contact of the plate to a thermal cycling means; a rigid well-forming structure placed above or on the top side of the bottom layer defining single wells and providing the side walls of the wells, wherein the well-forming structure comprises rigid substantially horizontal well-covering areas that cover the liquid sample comprised in the wells at the top side of the liquid sample, the well-forming structure comprises filling channels having filling openings and venting channels having venting openings for enabling filling of the wells with liquid sample, wherein an opening area of each of the filling openings is larger than an opening area of each of the venting openings, and each filling opening and venting opening of a well is placed adjacent a side wall of the well; and a substantially plane cover placed above or on the top side of the well-forming structure, wherein the cover provides a sealing cover of the wells and a thermal insulating air distance between the well-covering areas of the well-forming structure and the cover.

In still another embodiment, a high-density multiwell-plate for performing thermocycled amplification reactions of polynucleotides in liquid samples is disclosed. The plate comprises a plurality of reaction wells for thermal processing and nucleic acid amplification of the liquid samples and said plate being designed to be thermally processed by a thermal cycling means of an apparatus for analyzing the liquid samples; a substantially plane bottom layer for providing a thermal contact of the plate to a thermal cycling means; a rigid well-forming structure placed above or on the top side of the bottom layer defining single wells and providing the side walls of the wells, wherein the well-forming structure comprises rigid substantially horizontal well-covering areas that cover the liquid sample comprised in the wells at the top side of the liquid sample, the well-forming structure having for each of the wells a filling opening and a venting opening located in a filling area which is located aside the horizontal cross section of the well, wherein the filling area corresponds to the area neighbored to the well according to the pitch of the plate, so that the filling areas and the horizontal cross sections of the wells of at least one of the columns and the rows of wells of the plate are arranged in alternating sequences; and a substantially plane cover placed above or on the top side of the well-forming structure, wherein the cover provides a sealing cover of the wells and a thermal insulating air distance between the well-covering areas of the well-forming structure and the cover.

Further details and advantages of the present invention are illustrated in the following based on an exemplary embodiment making reference to the attached drawings.

DETAILED DESCRIPTION

Figure 1:
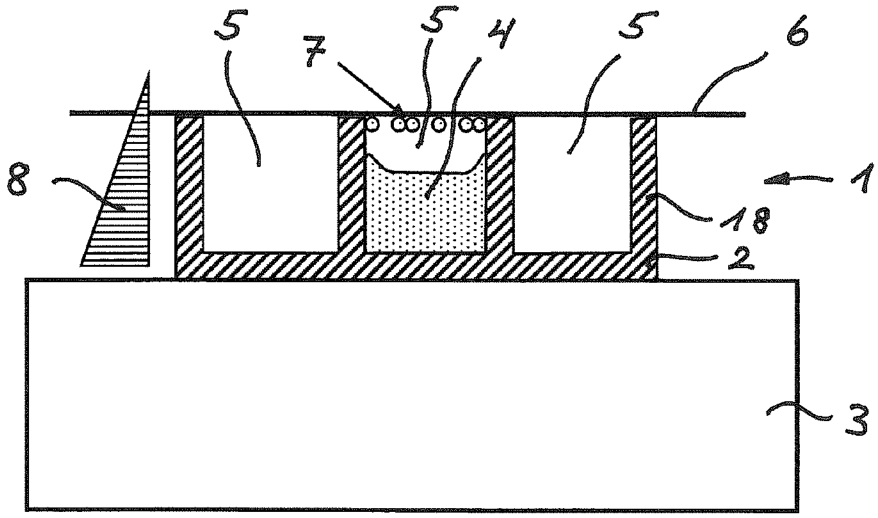
Fig. 1 (PRIOR ART)
FIG. 1 illustrates a schematic cross section of a high-density multiwell-plate according to the prior art.

The following description of the embodiments is merely exemplary in nature and is in no way intended to limit the invention, its application, or uses. For example, the present invention may find utility in a wide variety of applications, such as in connection with Polymerase Chain Reaction (PCR) measurements; ELISA tests; DNA and RNA hybridizations; antibody titer determinations; protein, peptide, and immuno tests; recombinant DNA techniques; hormone and receptor binding tests; and the like. Additionally, the present invention is particularly well suited for use with luminescence, colorimetric, chemiluminescence, or radioactivity measurement such as scintillation measurements. Although the present invention will be discussed as it relates to Polymerase Chain Reaction measurements, such enabling discussion should not be regarded as limiting the present invention to only such applications.

Embodiments of the present invention are directed to a multiwell-plate which may be used in methods which comprise the amplification of polynucleotides.

One embodiment of the invention is directed to a disposable high-density multiwell-plate for performing thermocycled amplification reactions of polynucleotides in liquid samples, said plate comprising a plurality of reaction wells for thermal processing and nucleic acid amplification of the liquid samples and said plate being designed to be thermally processed by a thermal cycling means of an apparatus for analyzing the liquid samples. Usually such a plate is intended to be operated in a nucleic acid amplification apparatus for analyzing liquid samples containing a nucleic acid by a nucleic acid amplification technique, particularly a Polymerase Chain Reaction Technique (PCR) analysis, more particularly a quantitative real-time-PCR (TaqMan™ (Applied Biosystems)—PCR or Hybridization-Probe-PCR) analysis.

Another embodiment of the present invention relates to multi-well microtiter plates. Embodiments of such plates include those useful for conducting thermocycled amplification of polynucleotides, including polymerase chain reaction.

As referred to herein, "polynucleotide" refers to naturally occurring polynucleotides (e.g., DNA or RNA), and analogs thereof, of any length. As referred to herein, the term "amplification" and variants thereof, refers to any process of replicating a "target" polynucleotide so as to produce multiple polynucleotides that are identical or essentially identical to the target in a sample, thereby effectively increasing the concentration of the target in the sample.

As used herein with the embodiments of the invention, amplification of either or both strands of a target polynucleotide comprises the use of one or more nucleic acid-modifying enzymes, such as a DNA polymerase, a ligase, an RNA polymerase, or an RNA-dependent reverse transcriptase. Amplification methods among those useful herein include methods of nucleic acid amplification known in the art, such as Polymerase Chain Reaction (PCR), Ligation Chain Reaction (LCR), Nucleic Acid Sequence Based Amplification (NASBA), self-sustained sequence replication (3SR), strand displacement activation (SDA), Q (3 replicase) system, and combinations thereof.

A multiwell-plate meeting the above mentioned needs noted in the background section is provided by an embodiment according to the invention wherein a high-density multiwell-plate for performing thermocycled amplification reactions of polynucleotides in liquid samples is disclosed. The plate comprising a plurality of reaction wells for thermal processing and nucleic acid amplification of the liquid samples and said plate being designed to be thermally processed by a thermal cycling means of an apparatus for analyzing the liquid samples, wherein the plate comprises a substantially plane bottom layer for providing a thermal contact of the plate to a thermal cycling means, a rigid well-forming structure placed above or on the top side of the bottom layer defining single wells and providing the side walls of the wells, wherein the well-forming structure comprises rigid substantially horizontal well-covering areas that cover the liquid comprised in the wells at the top side of the liquid, and a substantially plane cover placed above or on the top side of the well-forming structure, wherein the cover provides a sealing cover of the wells and a thermal insulating air distance between the well-covering areas of the well-forming structure and the cover.

Embodiments of the invention is based on the finding that it is possible to avoid a high thermal difference between the bottom layer and the cover of the plate by using a rigid-well forming structure placed above or on top of the bottom layer covering the samples when they are filled into the wells and by having a thermal insolating air gap between the well-covering areas of the well-forming structure and a cover. By this it is not required to heat the cover in order to avoid condensation of liquid, and further the bottom layer can be made very thin in order to optimize the thermal coupling between the sample and the thermal cycler. However, in order to achieve an optimal temperature gradient it may be useful to heat the cover to a temperature between annealing and melting temperature of the PCR, i.e. between 50° C. and 90° C., preferably near 70° C.

Because the wells in a plate according to an embodiment of the invention are covered or closed on top by the well-forming structure, the well-forming structure comprises according to a preferred embodiment filling channels and venting channels for enabling filling of the wells with liquid.

Preferably, for a liquid volume of 2 microliters, the filling opening volume is only 4 microliters. Prior art devices perhaps used a 3 microliters sample to a 100 microliters containment volume. Further, lowering the volumes of reagent has the advantage of saving costs. Yet further it enables the number of apertures in a given size of reaction plate to be increased, which allows an increased throughput of tests at low reagent volumes to be fully realized. This also increases the number of tests achievable when only a limited original sample, for example of DNA or RNA, is available to work with.

Preferably the well-forming structure is formed only of chemically stable materials, for example polymers such as polypropylene or polycarbonate. Preferably the well-forming structure is manufactured by injection molding. Suitable plastic materials, which are inert with respect to the sample liquid and to reagents, are for example polypropylene, polyethylene, polystyrene, polycarbonate and polymethylmethacrylate. Preferably a thermo-plastic material is used, especially polypropylene. Polypropylene is particularly suitable since it is injection moldable, inert with respect to reagents, heat stable at reaction temperatures, for example from 0° C. to 95° C. It also has some heat conductivity so that heat can be transferred from well to well in order to achieve a uniform temperature in the well-forming structure and in the samples in the wells. Specific types of polypropylene with a high thermal conductivity are available and therefore preferred for the bottom layer of the disposable if the disposable is formed out of multiple layers.

Polypropylene is available optically clear or optically opaque which is useful for fluorescent analysis of the reagent sample post-detection. Post welding it further has minimal cross talk from adjacent reaction wells due to the sealing weld around each reaction well. Yet further, polypropylene is capable of high thermal flux and can also be supplied in films of between 10 and 120 micrometers thickness. It also can be frozen for storage purposes, e.g. taken down to temperatures of −20° C. and −70° C. It is preferred when the well-forming structure is made from one piece, but it can also be composed of several pieces or several layers.

Preferably the cover film is formed of a transparent plastics material. The film is preferably optically clear with very low distortion or cross talk. This allows both manual (i.e. human) and automated (i.e. machine) inspection of, for example, each PCR. However, for sensors operating using UV or IR sensation, for example, i.e. outside the visible range, the film need only be transparent for the appropriate electromagnetic wavelength used. Using laser welding to attach the film may in some embodiments also increase (improve) the fluorescent imaging signal to noise ratio due to the better optical parameters achieved with the thereby attached film compared to thermal welding due to simplified optical properties of the planner reaction plate.

Preferably in one embodiment, the bottom layer and/or the well-forming structure, except an optical window required for optical inspection, is black. This is to prevent cross interference, in automated inspection apparatus, from, for example, PCRs in adjacent wells. The bottom layer and/or the well-forming structure could be otherwise light absorbent to the relevant frequency of the EM radiation used by the automated inspection equipment. The absorbency also prevents internal reflections within the aperture, e.g. from side walls thereof, from interfering with automated inspection. In other embodiments it may also be preferable if the bottom layer is white or highly reflective in order to achieve a high optical, e.g. fluorescence signal.

In use, one or more reagent and one or more samples (multiplexed) will be retained within the wells. The cover film may be pierceable to allow the reagent and sample, for example in fluid form, to be inserted into or removed from the wells, if required. However, in this case the pierced cover would not be vapor-tight upon thermal cycling of the plate. Therefore it is preferred when the cover is fixed and placed above or on the top side of the well-forming structure after the wells have been filled in order to achieve a tight sealing of the wells. The cover can be fixed by a suitable method like heat sealing, thermal welding, hot gluing, gluing, bonding or laser welding.

Preferably the weld around the well is continuous to seal the cover to the aperture well-forming structure around the periphery of a well at the end thereof. However, when channels or grooves are provided, the weld would then preferably be continuous along the periphery of the channels or grooves and the apertures connected thereby.

Preferably the multiwell-plate is less than 4 mm thick. More preferably the multiwell-plate is approximately 0.5 mm thick. Most preferably the multiwell-plate is approximately 1.3 mm thick. The multiwell-plate could even be about 0.2 mm thick. Such thin plates may be formed or cut from continuous webs, for example off a roll of aperture material. This could give advantageous handling characteristics in an automated manufacturing and processing apparatus and higher throughputs could be achieved.

The apparatus for analyzing the samples in the multiwell-plate may comprise means for filling the wells or each well at least partially with a reagent and sample, such as filling means known in the prior art, e.g. robotic syringe injectors, piezo electric dispensers, pin dispensing, peristaltic pumps, positive displacement dispensers or capillary dispensers.

The apparatus may comprise means for holding the multiwell-plate at the time of welding, e.g. using a vacuum bed, to allow accurate transmission welding.

The apparatus may also comprise means to carry out reactions using the multiwell-plates e.g. plate handlers and heating means for applying heat to the reagent and sample within the apertures through conduction and/or radiation through the film. The handlers may need to rotate the plates to position the appropriate side thereof (with the film) against the heating means. Suitable plate handlers and heating means are already known in the prior art, for example robotic handlers, hotplates and water baths.

The apparatus may also comprise sensing means to inspect the contents of the wells during or after the reaction has been effected, such as means using fluorescence, reflectance or the like. The sensing means can view within the apertures, at the PCR for example, through the bottom layer or the cover.

Embodiments of the present invention allow the reduction in costs to about $0.10 per reaction by reducing the well or reaction volume of 10 μl to 2 μl per reaction. To put this achievement into perspective, the required scale of genotyping in just a single pharmaceutical company can easily run to 100 million reactions per year, thus costing approx. $50,000,000. By reducing the volume size to just two microliters, this cost could potentially be reduced to $10,000,000. The typical well volumes of a micro-well plate according to the invention is 1 μl to 2 μl for the "open type" and 0.2 μl to 1 μl for the type with microfluidic filling structures.

Embodiments of the present invention could also provide perhaps a 16 fold increase in throughput due to an increased number of wells per reaction plate at an affordable cost. Current 7700™ technology would be incapable of the required pharmaceutical high throughput genotyping due to high equipment cost and high reagent costs.

The new high well density and low well volume reaction plates of the present invention enable the genotyping field to be substantially expanded, using a robust and approved technique already established throughout the scientific community.

In order to analyze large numbers of fluid samples by a nucleic acid amplification technique like polymerase chain reaction technique speed and cost of an analysis are important aspects of sample holding and processing devices.

Embodiments of the present invention therefore provide a multiwell-plate suitable for analyzing a fluid sample at low cost and within a conveniently short time. Further disadvantages of the prior art addressed by the present invention are the aspects of easy manufacturing, easy to use in an automatic processing device, in particular with respect to the aspects of thermal processing and the avoiding of biohazard risks by providing a disposable multiwell-plate for processing.

FIG. 1 shows a cross section of a multiwell-plate 1 according to the prior art. It has a bottom 2 produced by injection molding, wherein the bottom is relatively thick (in the range of 0.5 to 1.0 mm). The bottom 2 is made of the same material as the complete multiwell-plate 1. This results in a low thermal conductivity from the flat block-cycler 3, which may also be a water bath, through the bottom 2 of the multiwell-plate 1 into the liquid samples 4 comprised in the wells 5 of the multiwell-plate 1. Therefore the processing times for the thermocycle process are high.

Further, the cover 6 (top layer) placed on top of the wells 5 and closing the wells 5 has to be heated. If the cover 6 would not be heated the following disadvantages result. The first is a high temperature decrease in the liquid sample 4 of a well 5 from the bottom 2 into the direction of the cover 6 which considerable reduces the performance of the PCR analysis. The second disadvantage is a condensation 7 of the liquid sample 4 comprised in the gas volume of a well 5 on the under side of the cover 6 directed to the liquid sample 4. The upper side of the cover 6 is at room temperature. The resulting thermal gradient 8 is illustrated by a wedge. Because the optical detection of the liquid sample 4 processed in the well 5 of a plate 1 is performed through the cover 6 such a condensation 7 would interfere the optical detection. As a consequence, the cover 6 has to be heated in order to avoid these disadvantages. In view of the fact that the size of the wells 5 is very small and also the optical detection has to be performed through the cover 6 this is a difficult task and requires costly measures. In addition a constantly heated lid forms a thermal gradient between the cover and the bottom of the well, in a way that most of the liquid is above the target temperature.

Figure 2:
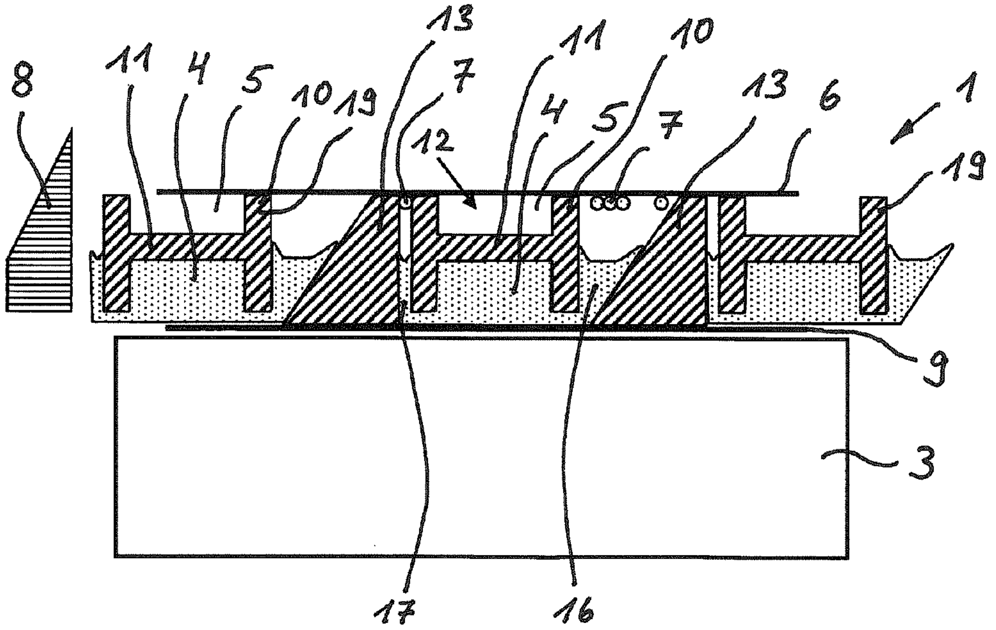
FIG. 2 illustrates a schematic cross section of a first embodiment of a multiwell-plate according to the invention.

These disadvantages are avoided by a multiwell-plate 1 according to the invention shown in FIG. 2. It is a high-density multiwell-plate 1 for PCR. The wells 5 of this multiwell-plate 1 are covered on the top side by a transparent cover 6 for enabling optical detection and comprise a filling and venting structure 13 for filling the wells 5 with liquid sample 4, which filling and venting structure 13 will be explained later with reference to FIGS. 3 and 4.

The multiwell-plate 1 is used for performing thermo cycled amplification reactions of polynucleotides in liquid samples 4. For this purpose the multiwell-plate 1 comprises a plurality of reaction wells 5 for thermal processing and nucleic acid amplification of the liquid samples 4. The plate 1 is designed to be thermally processed by a thermal cycling means of an apparatus for analyzing the liquid samples 4, e.g. by a block-cycler 3 which can be heated and/or cooled or a water bath. The plate 1 comprises a substantially plane bottom layer 9 for providing a thermal contact of the plate 1 to the block-cycler 3 and a rigid well-forming structure 10 placed above or on the top side of the bottom layer 9 defining single wells 5 and providing the side walls of the wells 5, wherein the well-forming structure 10 comprises rigid substantially horizontal well-covering areas 11 that cover the liquid sample 4 comprised in the wells 5 at the top side of the liquid sample 4. Further, the multiwell-plate 1 comprises a substantially plane cover 6 placed above or on the top side of the well-forming structure 10, wherein the cover 6 provides a sealing cover of the wells 5 and a thermal insulating air distance 12 between the well-covering areas 11 of the well-forming structure 10 and the cover 6.

The top side of the cover 6 is at room temperature and the resulting thermal gradient 8 is again illustrated by a wedge. The cover 6 and the air distance 12 provide an insulating air layer between the top side of the liquid sample 4 (or the top side of the well-covering areas 11) and the bottom side of the cover 6 which reduces the thermal difference between the bottom and the top of the liquid sample 4. An advantage of the multi-well plate 1 according to the invention is that the liquid sample 4 comprised in a well 5 is almost completely surrounded by rigid walls which reduces condensation (see numeral 7 in FIG. 1) of the liquid sample 4 from the vapor state and therefore improves the quality of the optical path for detecting the liquid sample 4 via an optical path through the cover 6 and the well-covering area 11 of the well-forming structure 10.

The well-forming structure 10 is preferably placed on top of the bottom layer 9 so that the bottom layer 9 provides the bottom of the wells 5. In a preferred embodiment the cover 6 and/or the bottom layer 9 for sealing the wells 5 tightly is a thin sheet material, i.e. a plastics foil. The cover 6 or in particular the bottom layer 9 may comprise several layers, in particular two layers. According to a preferred embodiment the bottom layer 9 comprises an upper layer made of a plastics material (which is inert with respect to the liquid sample 4) directed to the liquid sample 4 and a lower layer made of a metal (preferably aluminum) directed to the thermal cycling means. The lower layer is preferably thicker than the upper layer.

The lower layer provides an efficient way for transporting heat to the liquid sample 4 or away from it by the block-cycler 3. For heating or cooling of the sample bottom layer 9 can be connected to a heating or cooling area of an analysis apparatus. Preferably, the thickness of the bottom layer 9 is as small as possible while still ensuring sufficient mechanical strength for reliably sealing the various well 5 of the plate 1. The lower the thickness of the bottom layer 9 is the lower is its thermal capacity and the higher is the heat transfer rate. A low thermal capacity, a high heat transfer conductivity and high heat transfer rate are advantageous as they enable faster heating and cooling of the plate 1, respectively of fluids therein.

Generally, the thickness of the bottom layer 9 should not exceed 1 mm, preferably be below 500 μm. In order to ensure sufficient mechanical strength for a reliable sealing of the wells 5 and of the channels in the plate 1 the thickness should be at least 20 μm. Particularly advantageous is a thickness of 25 μm to 350 μm, especially of 30 μm to 200 μm.

Aluminum is particularly well suited as material for the lower layer of the bottom layer 9 as it has a very low thermal capacity. Of course, other materials can also be used. The thickness of the bottom layer 9 layer is preferably 20 μm to 400 μm, especially 20 μm to 200 μm.

As the function of the upper layer of the bottom layer 9 is mainly to prevent contact between liquid sample 4 and the lower layer it is advantageous to provide the upper layer with a thickness as small as possible while still ensuring a continuous layer. The thickness of the upper layer should therefore be less than 300 μm, preferably less than 200 μm, especially less than 100 μm. Particularly preferred is a thickness of the upper layer of 0.1 μm to 80 μm.

In preferred embodiments the bottom layer 9 is a composite foil comprising the upper layer and the lower layer. The upper layer can be laminated to the lower layer or sprayed, painted or, for example, vapor deposited on the lower layer. More layers can be added to the bottom layer 9, for example a coat of paint to protect the lower layer. According to a preferred embodiment the cover 6 and/or the bottom layer 9 is a composite foil. The thermal conductivity of the bottom layer 9 is preferably at least 20 $Wm^{-1}K^{-1}$, preferably at least 200 $Wm^{-1}K^{-1}$.

The bottom layer 9 and the cover 6 can be fixed to the plate 1 or the well-forming structure 10 by means of suitable bonding procedures, e.g. by thermal sealing or by use of an adhesive, e.g. a polyurethane or polymethylmethacrylate adhesive. Preferably, the bottom layer 9 and the cover 6 are bonded using thermal bonding or welding, for example by ultrasonic welding or laser welding. Welding is most feasible if the upper layer of the bottom layer 9 consists of the same material as the well-forming structure 10, e.g. polypropylene.

As can be seen in FIG. 2, the well-forming structure 10 comprises webs 19 (raised sections) that project above the well-forming structure 10 for providing the thermal insolating air distance 12 between the well-covering areas 11 of the well-forming structure 10 and the cover 6, wherein the cover 6 is placed on top of the webs 19 and fixed to the webs 19.

The foil on the bottom of the well-forming structure 10 is preferably an aluminum-polypropylene foil having a good thermal conductivity. Preferably the polypropylene side of the bottom layer 9 is directed towards the liquid sample 4, because in this case it can be best fixed to the well-forming structure 10.

Figure 3:
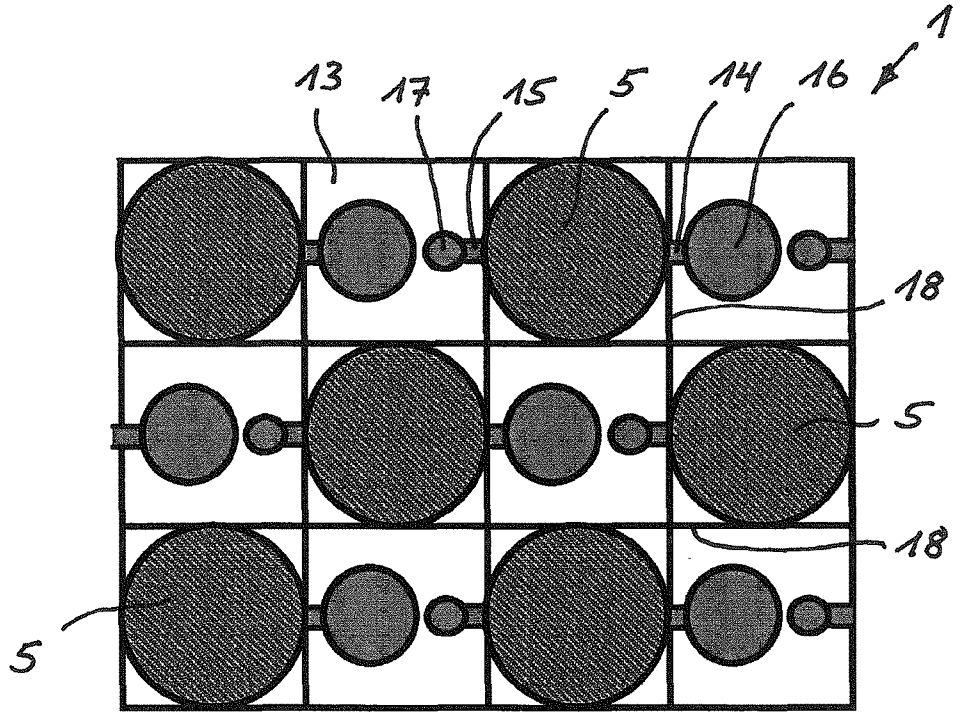
FIG. 3 illustrates a schematic top view of the embodiment of FIG. 2.
Figure 4:
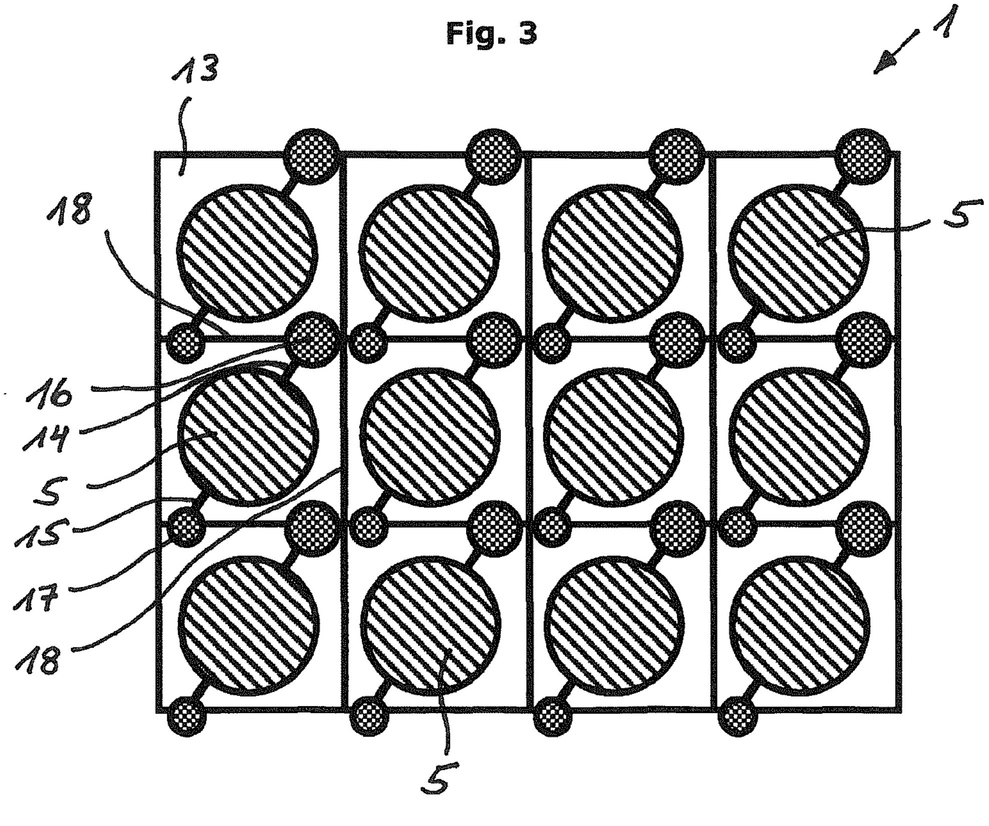
FIG. 4 illustrates a schematic top view of a second embodiment of a multiwell-plate according to the invention.

FIG. 3 illustrates a schematic top view of the multiwell-plate 1 of FIG. 2. The plate 1 comprises a filling and venting structure 13 for filling the wells 5 with liquid sample 4. The filling channels 14 and the venting channels 15 for enabling filling of the wells 5 with the liquid can be comprised in the plate 1 or the well-forming structure 10. In a first embodiment the well-forming structure can comprise individual filling channels 14 and venting channels 15 for individually filling single wells 5 as shown in FIGS. 3 and 4. Preferably, the filling channels 14 comprise a filling opening 16 and the venting channels 15 comprise a venting opening 17 for enabling filling of the wells 5 with liquid sample 4. For practical purposes it is preferred for an easy filling of the wells 5 when the opening area of the filling opening 16 is larger than the opening area of the venting opening 17. The bigger the filling openings 16 are, the easier it is to provide liquid into the filling opening 16 by pipetting.

The well-forming structure 10 and the filling and venting structure 13 can preferably be provided in different manners. One is shown in FIG. 3, wherein only every second well 5 is used for PCR, wherein in the neighbored well the filling structure of a well 5 and the venting structure of another well 5 is placed. In the embodiment of FIG. 3 the filling opening 16 and the venting opening 17 of a well 5 are located in a filling area, which is located aside the horizontal cross section of the well 5, wherein the filling area corresponds to the area neighbored to the well 5 according to the pitch of the plate 1, so that the filling area and the horizontal cross sections of the wells 5 of the columns and/or of the rows of wells 5 of the plate 1 are arranged in alternating sequences. In another embodiment shown in FIG. 4 the filling and venting structure 13 of a well 5 is placed in a well 5, in particular in a corner of the horizontal cross section or near or on a side wall 18 of the well 5.

The multiwell-plate 1 comprises a rigid well-forming structure 10 made by injection molding comprising the filling and venting channels. The bottom of the multiwell-plate 1 is preferably made by a foil with a high thermal conductivity, e.g. aluminum or polypropylene. For performing a PCR-analysis the wells 5 are filled with liquid sample 4 and covered by a cover 6.

According to FIG. 3 in the embodiment of FIG. 2 the standard pitch (well to well step size or distance) is used for placing the filling and the venting structure 13 in the plate 1, wherein only every second well 5 in a column or row of the well is used for filling with liquid sample 4 and every other well is used for placing the filling and venting structure 13. By this the standard pitch can be maintained enabling use of the plate 1 in standard automatic filling devices. In case that the filling and venting structures 13 are placed in a corner of the wells according to FIG. 4 each well 5 can be used as a PCR chamber.

The underside of the well-covering areas 11 is preferably in contact to the liquid sample 4 comprised in the wells 5. However, in some embodiments also an air gap between the underside of the well-covering areas 11 and the liquid sample 4 comprises in the wells 5 may be possible. By the rigid substantially horizontal well-covering areas 11 comprised in the well-forming structure 10 the liquid sample 4 comprised in a well 5 is also covered on its top side by a rigid wall and not only by an air distance (gap) 12. This considerably reduces condensation of liquid on walls, in particular on the under side of the cover 6 thus enabling optical detection of the liquid through the cover 6 and the well-covering area 11 without disturbance by condensation, even in case that the cover 6 is not heated by a heating means.

The thermal insulating air distance 12 between the well-covering areas 11 of the well-forming structure 10 and the underside of the cover 6 and its combination with the well-covering areas 11 of the well-forming structure 10 reduces temperature differences also in case that the cover 6 is not thermally heated. Therefore, in embodiments according to the present invention a heating of the cover 6 is not mandatory. Further, the well-covering areas 11 of the well-forming rigid structure 10 define more precisely the optical detection path for detecting the reactions in the liquid sample 4 due to the plane and rigid well-forming structure 10. This is a more precise definition of the top surface of the liquid sample 4 when it is optically detected than in the prior art, wherein the surface tension of the liquid sample 4 and the adhesion of the liquid to the side walls 18 results in a curved surface of the liquid sample 4 with varying shape (see FIG. 1). Therefore, the optical detection of the liquid sample 4 according to the invention is more precise and has a better reproducibility.

A low thermal capacity for the device material of the plate 1 is advantageous and important since nucleic acid amplification techniques require as a general rule sample processing at temperatures above room temperature and polymerase chain reaction technique, for example, cycling between carefully controlled temperatures. The favorably low thermal capacity of a device according to the present invention provides for shorter times for heating or cooling sample liquid contained in the device and thus faster analysis.

Figure 5:
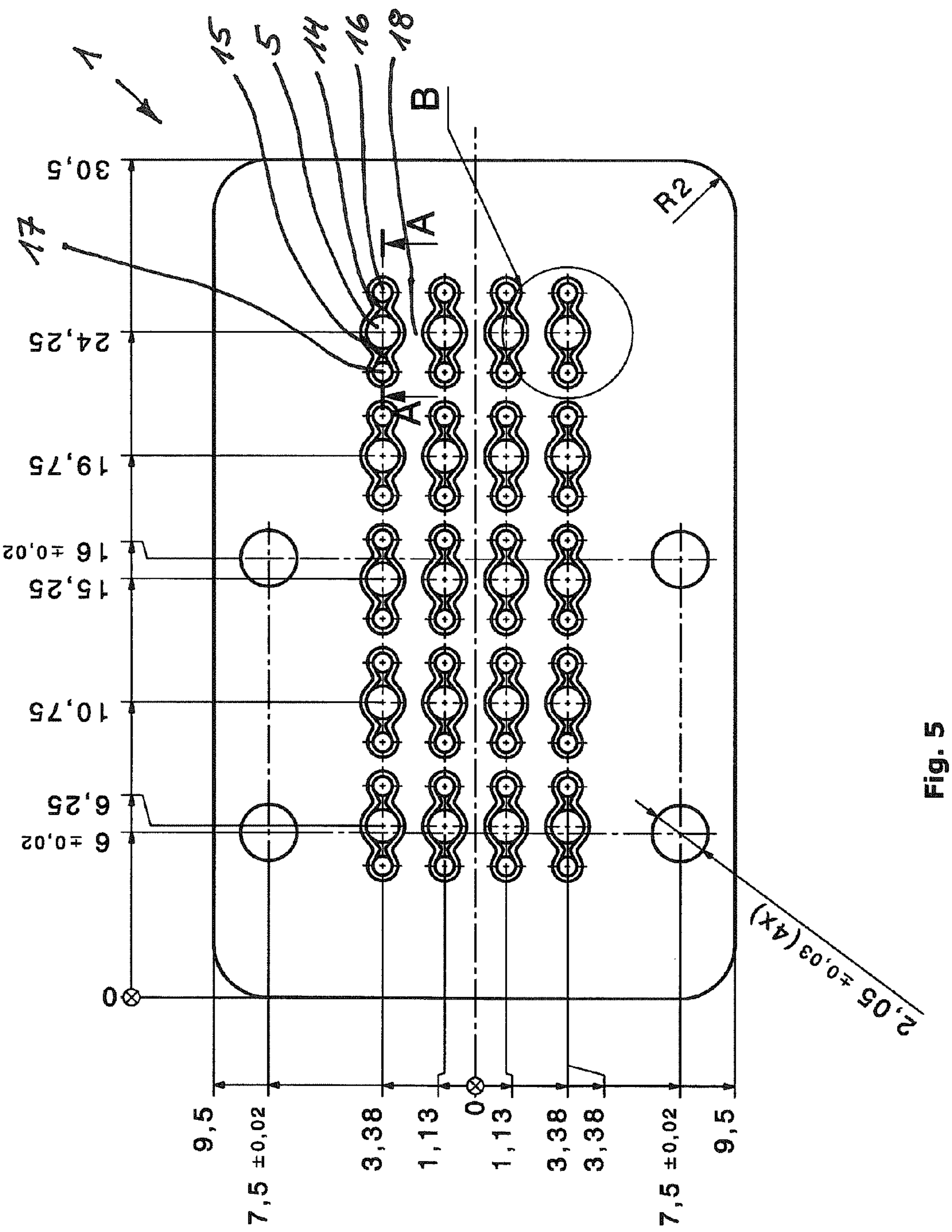
FIG. 5 illustrates a schematic top view of a third embodiment of a multiwell-plate according to the invention.

FIG. 5 illustrates a schematic top view of a second embodiment of a multiwell-plate 1 according to the invention. It is a prototype with less than the usual number of wells 5 comprised in practical embodiments and has been constructed for testing purposes to prove that the thermal insulating according to the invention as described in particular with respect to FIG. 2 is indeed working. The dimensions of this prototype are given in millimeters, as in all other figures comprised in the present application. The structure of the embodiment corresponds to the one shown in FIG. 3, wherein the original pitch is 2.25 mm, which is the pitch in a column of wells 5, but only the double pitch of 4.5 mm is used for arranging the wells 5 in the line spacing.

Figure 6:
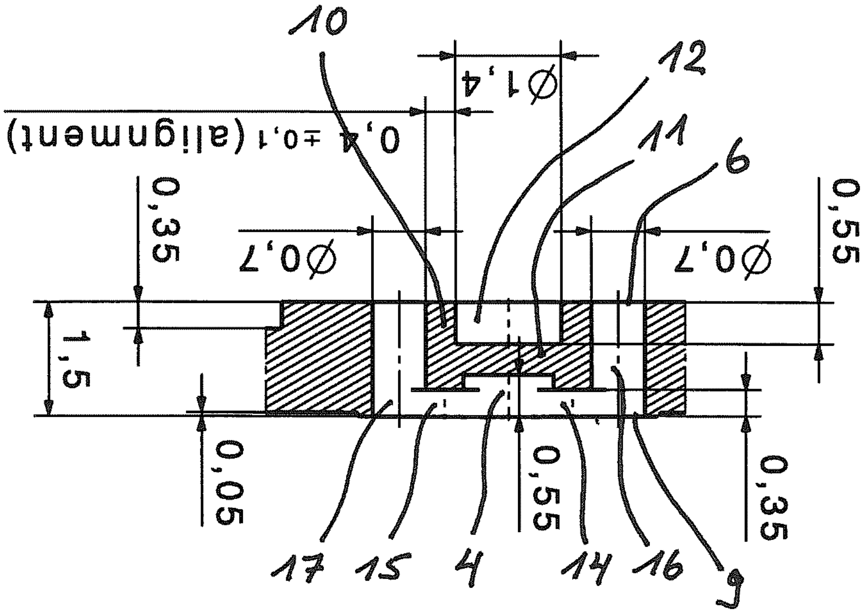
FIG. 6 shows a section A-A of FIG. 5.
Figure 7:
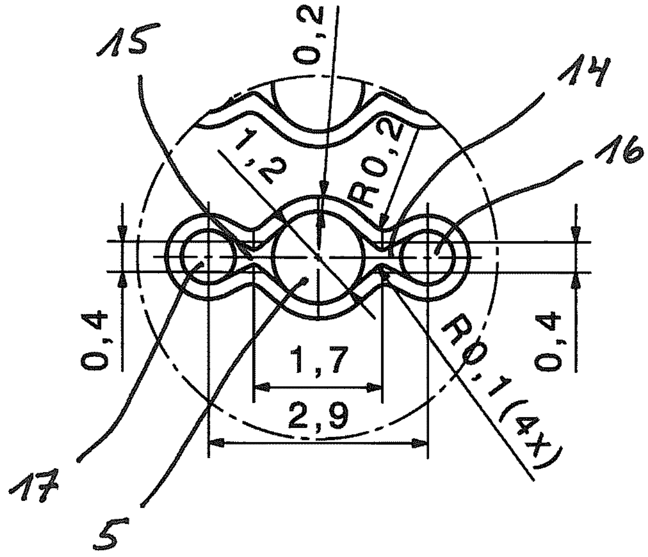
FIG. 7 shows a detail B of FIG. 5.
Figure 9:
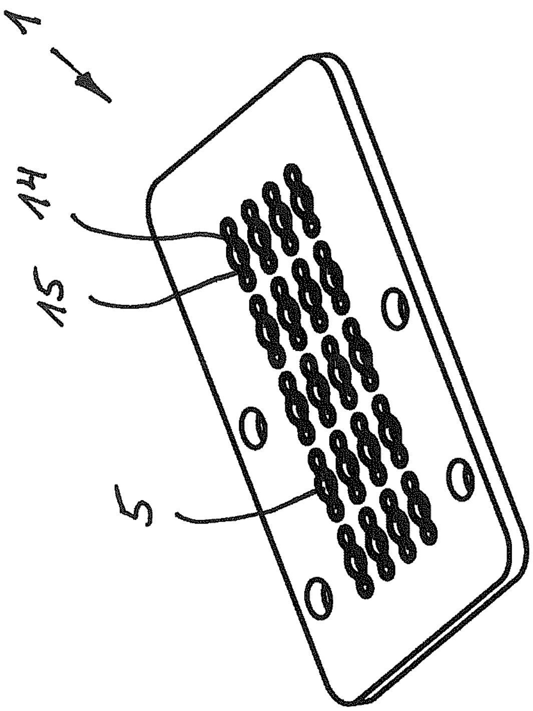
FIG. 9 shows another perspective bottom view of the embodiment of FIG. 5.
Figure 8:
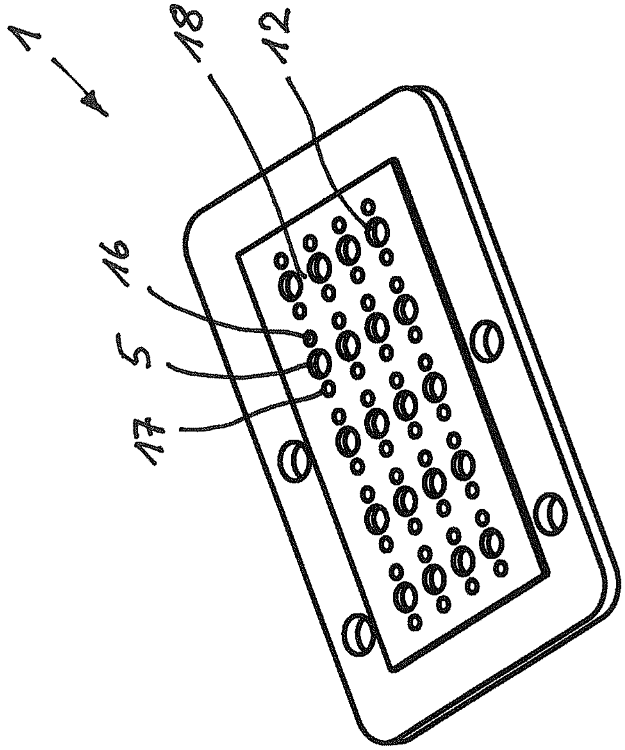
FIG. 8 shows a perspective top view of the embodiment of FIG. 5.

FIG. 6 shows a section A-A and FIG. 7 shows a detail B of FIG. 5. FIG. 8 shows a perspective top view and FIG. 9 shows a perspective bottom view of the embodiment of FIG. 5, without bottom layer.

Figure 10:
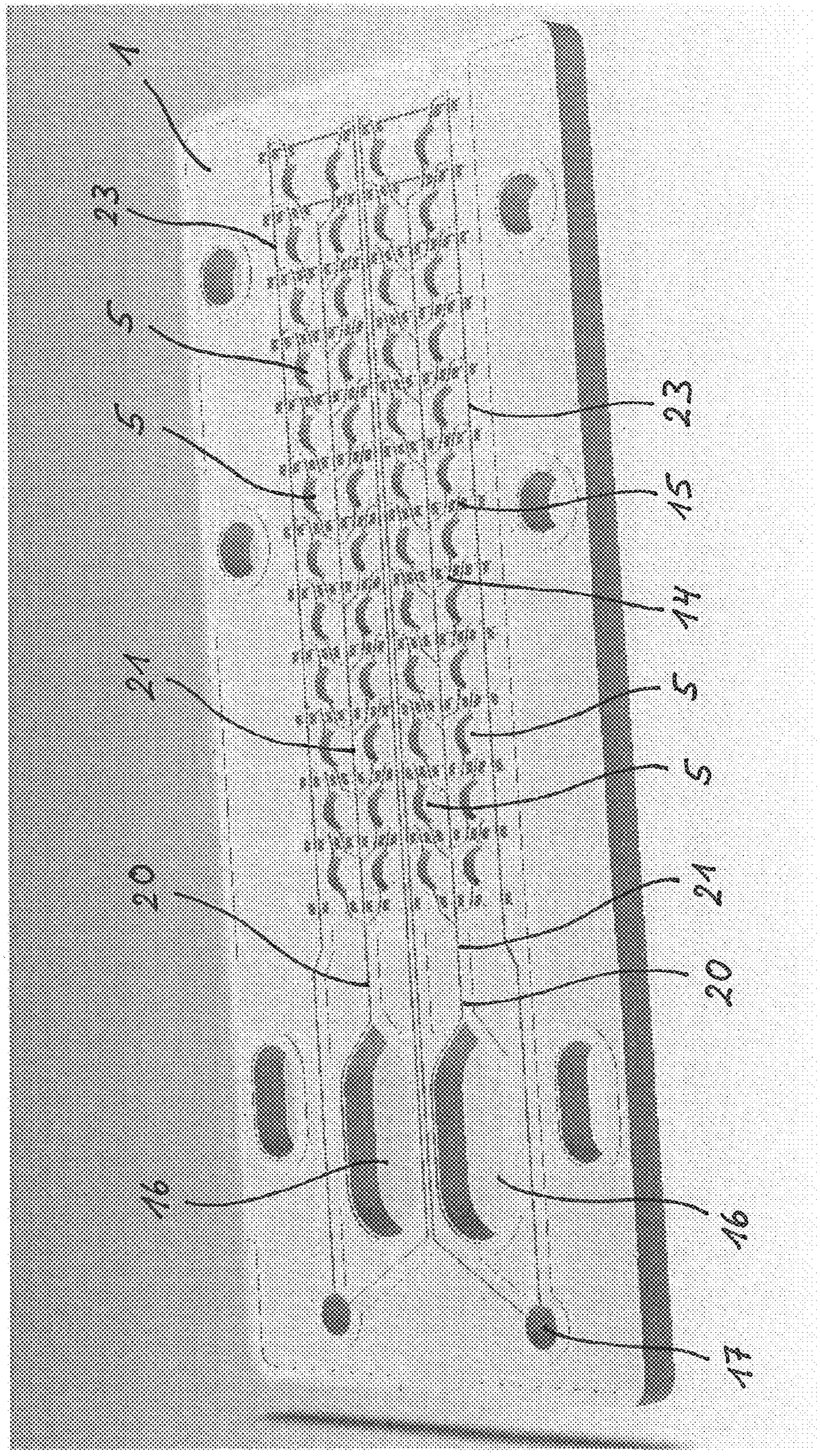
FIG. 10 shows a perspective bottom view of a fourth embodiment of a multiwell-plate according to the invention.

FIG. 10 shows a perspective bottom view of a fourth embodiment of a multiwell-plate 1 according to the invention. It shows a chip with 2×24 wells 5 in a 2.25 mm pitch with an integrated microfluidic sample distribution structure 20. The top side of the plate 1 shown in FIG. 10 is closed with a foil used as a bottom layer 9 after specific reagents have been placed in the wells 5. The liquid sample is later applied from the top side, which is placed in an upward direction via the two large filling openings 16.

The embodiment of FIG. 10 comprises a sample distribution structure 20 comprising a filing opening 16 (sample port) and a common filling channel 21 common to numerous wells 5 for filling numerous wells 5 with a liquid via the filling opening 16. The common filling channel 21 connects the filling opening 16 with numerous wells 5. The sample distribution structure 20 preferably is constructed such that the wells 5 are filled by a small differential pressure and/or capillary forces. The sample distribution structure 20 avoids the necessity to fill individual single wells 5 with a liquid sample by pipetting, because numerous or all wells 5 are filled via a single common filling opening 16. The embodiment shown in FIG. 10 comprises two common filling channels 21, each provided with a filling opening 16. Of course a similar common venting channel 23 can also be comprised.

In an embodiment comprising a sample distribution structure 20 the analytic tests of a well 5 may or should comprise specific reagents, e.g. primers or probes, preferably in a dried form in each well 5. Upon use of the plate 1 the liquid sample 4 is applied with generic PCR reagents via the central and common filling opening 16 (inlet, sample port). The liquid sample 4 then distributes via the common filling channel 21 and capillary forces into the individual wells 5. In some embodiments also a little pressure difference may be applied in order to enforce or assist the distribution of the liquid sample 4. In this case, the multiwell-plate 1 also comprises appropriate openings for applying the differential pressure.

The further construction of the multiwell-plate 1 of FIG. 10 corresponds to the other embodiments, in particular with respect to the insulation air distance 12 provided by the well-forming structure 10.

Figure 11:
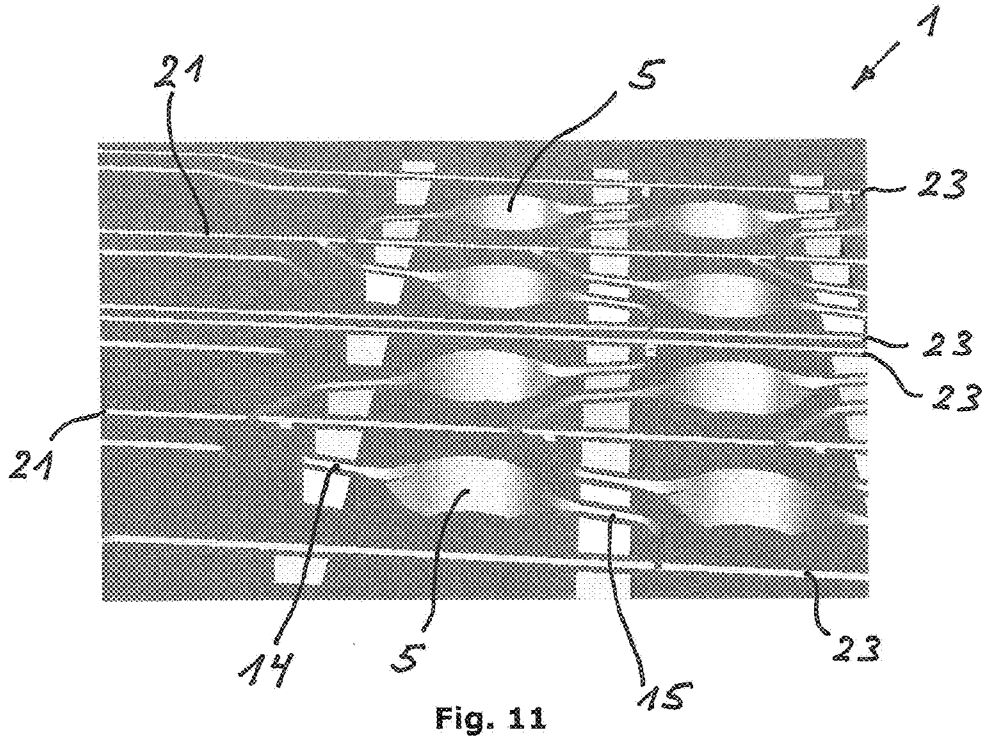
FIG. 11 shows a detail of FIG. 10.
Figure 12:
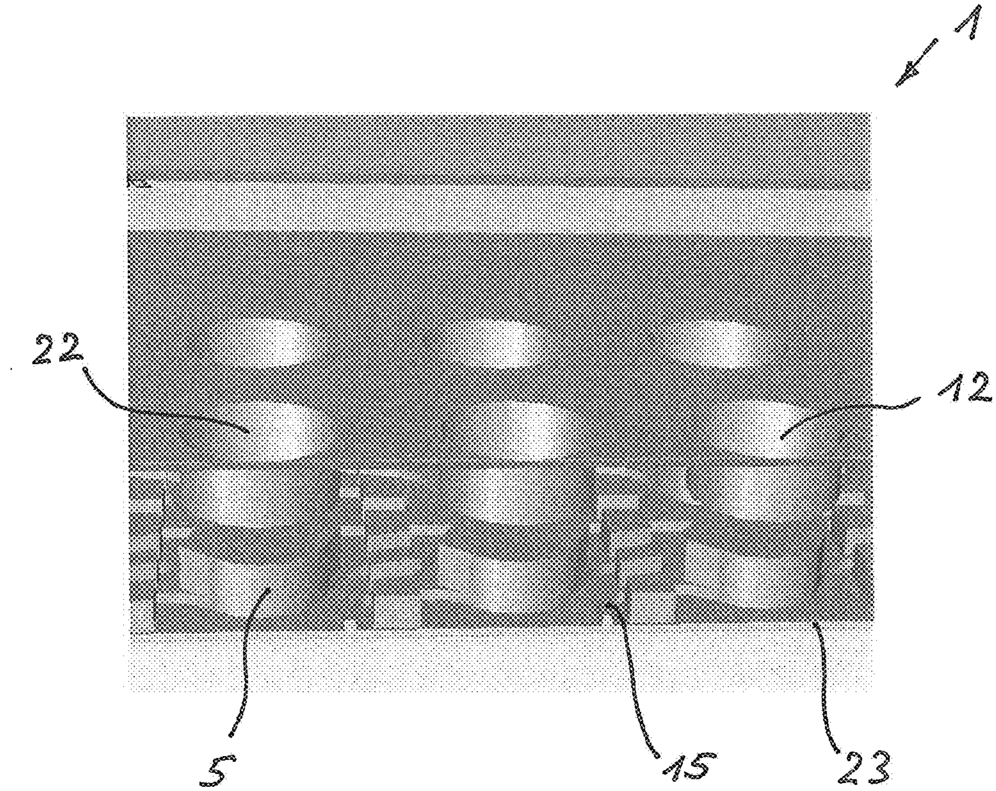
FIG. 12 shows another detail of FIG. 10.
Figure 13:
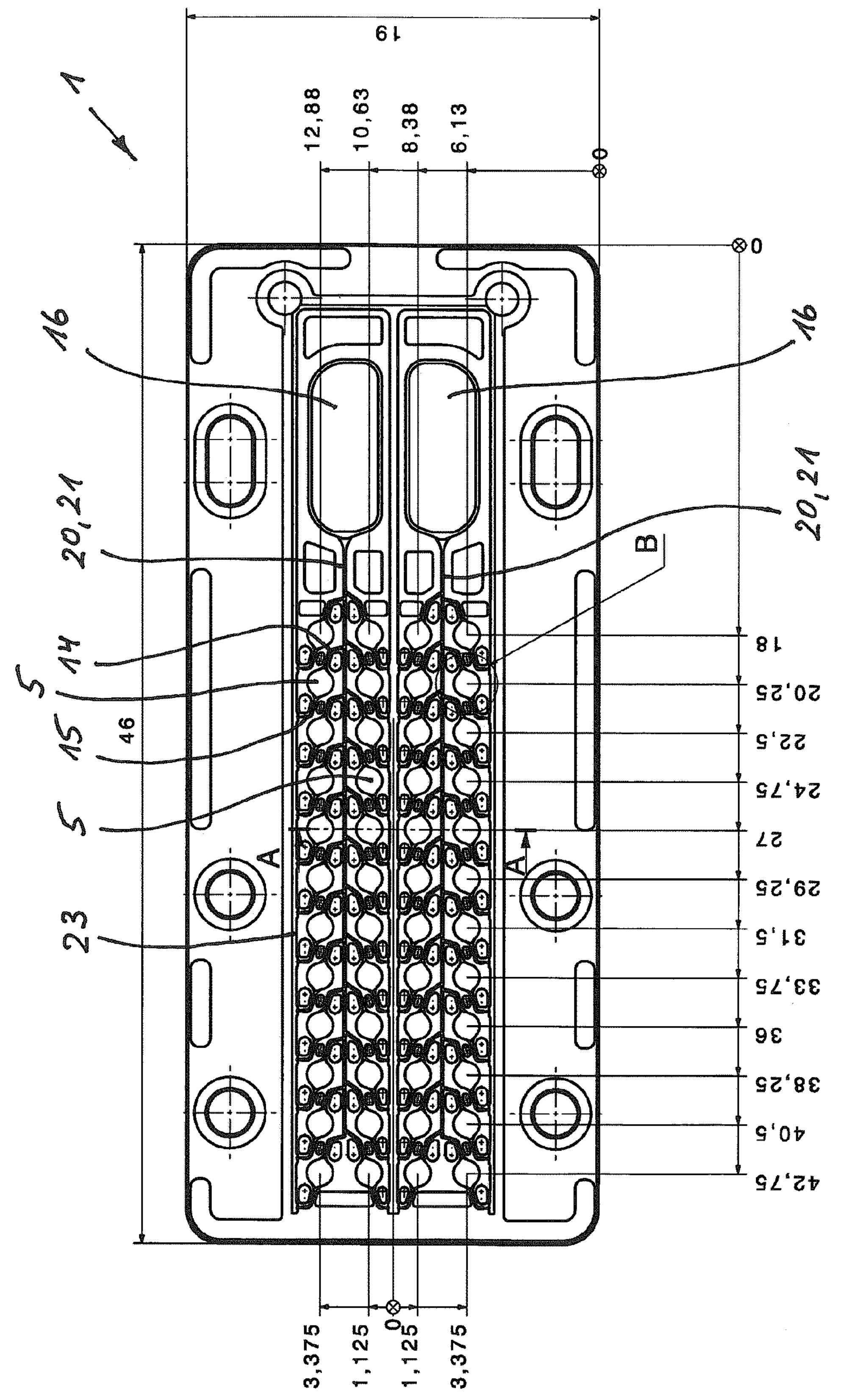
FIG. 13 shows a bottom view of the embodiment of FIG. 10.
Figure 14:
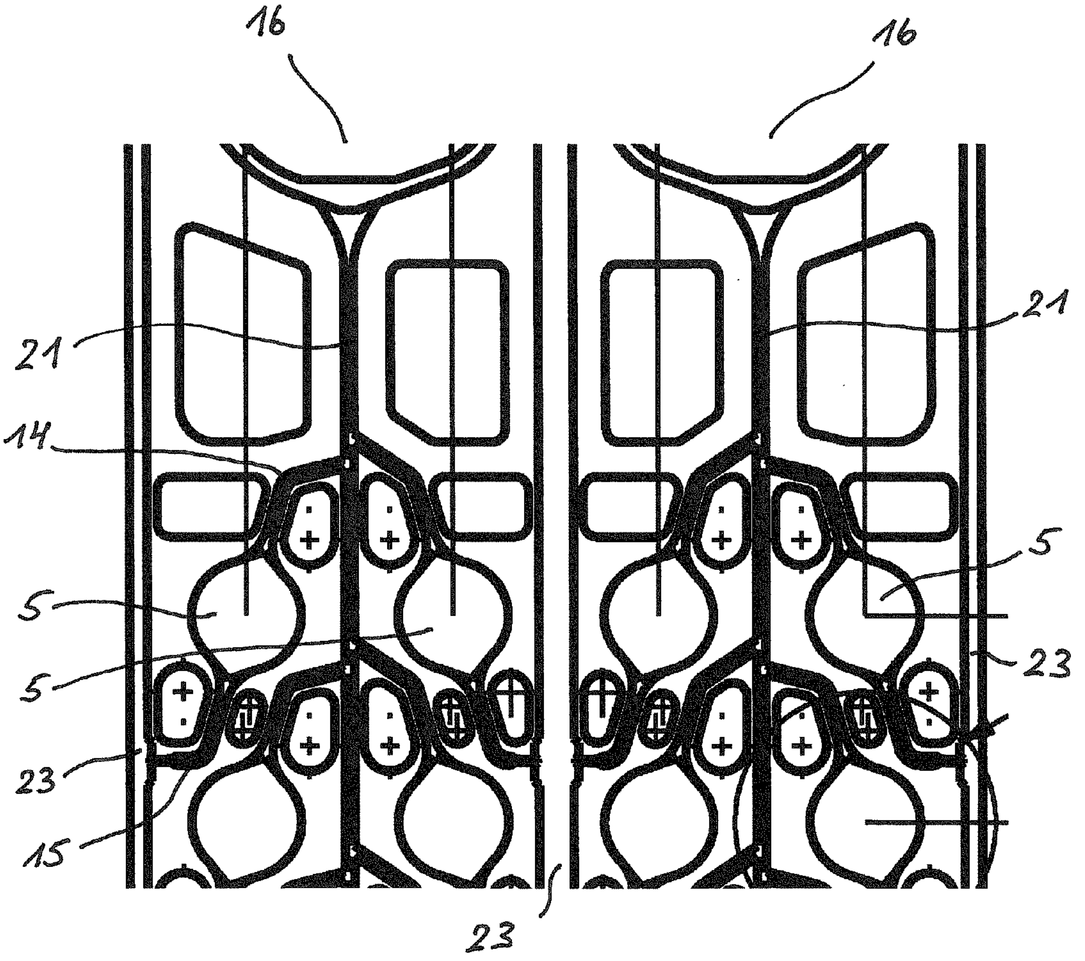
FIG. 14 shows a detail of FIG. 13.
Figure 15:
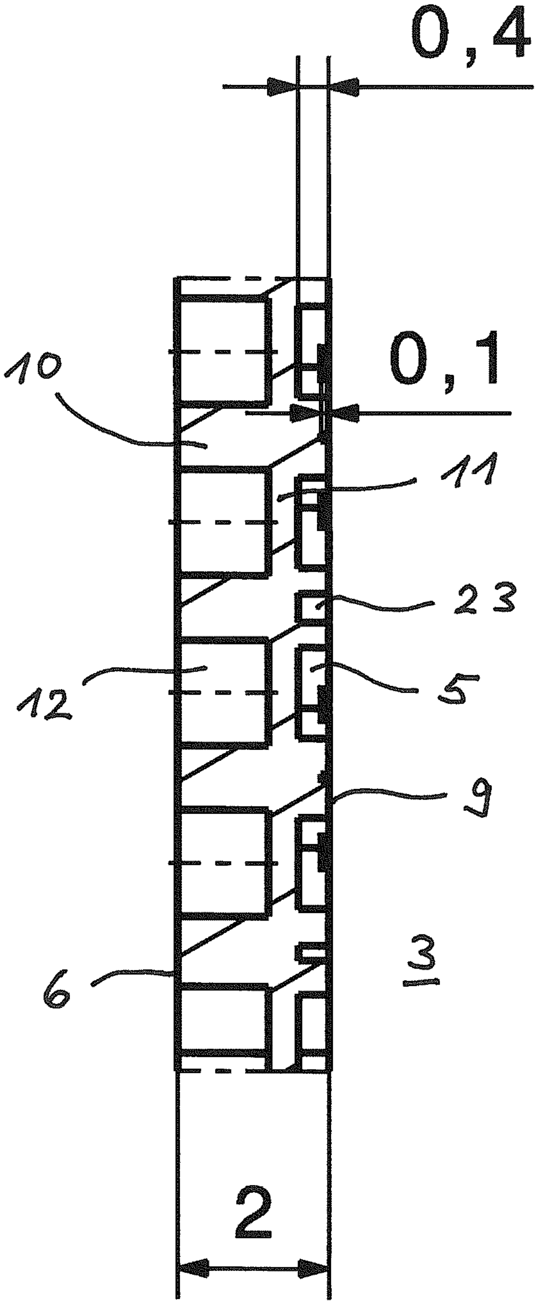
FIG. 15 shows a section A-A of FIG. 13.

FIG. 11 shows a in a detail of FIG. 10 the common filling channels 21 and the filling channels 14 connecting the wells 5 to the common filling channels 21, before the plate 1 is closed with bottom layer 9. FIG. 12 shows a partial cross sections of the multiwell-plate 1 of FIG. 10 with the sample distribution structure 20 on the bottom side and a cylinder shaped opening 22 on the upper side for providing a thermal insulation with respect to the optical interface, which is pressed against from the top side. FIG. 13 shows a bottom view of the embodiment of FIG. 10. FIG. 14 shows a detail of FIG. 13. FIG. 15 shows a section A-A of FIG. 13.

The above description and drawings are only to be considered illustrative of exemplary embodiments, which achieve the features and advantages of the present invention. Modification and substitutions can be made without departing from the spirit and scope of the present invention. Accordingly, the invention is not to be considered as being limited by the foregoing description and drawings, but is only limited by the scope of the appended claims.

What is claimed is:

1. A high-density multiwell-plate for performing thermocycled amplification reactions of polynucleotides in liquid samples, said plate comprising:

a plurality of reaction wells for thermal processing and nucleic acid amplification of the liquid samples and said plate being designed to be thermally processed by a thermal cycling means of an apparatus for analyzing the liquid samples;

a substantially planar bottom layer for providing a thermal contact of the plate to a thermal cycling means;

a rigid well-forming structure placed above the bottom layer defining single wells, wherein the well-forming structure comprises rigid substantially horizontal well-covering areas that cover the liquid sample comprised in the wells at the top side of the liquid sample;

a substantially planar cover placed above or on the top side of the well-forming structure, wherein the cover provides a sealing cover of the wells and a thermal insulating air distance between the well-covering areas of the well-forming structure and the cover; and at least a first filling and venting structure and a second filling and venting structure configured to be coupled to the substantially planar bottom layer and the substantially planar cover and configured so that the first filling and venting structure and the second filling and venting structure are located on opposite sides of the rigid well-forming structure, forming a filling channel comprising a filling opening and a venting channel comprising a venting opening and configured such that a liquid sample placed in the filling opening flows into the fluid channel and under the rigid well-forming structure to fill the well.

2. The plate according to claim 1, further comprising an optical window in the bottom layer, wherein the bottom layer is black except for the optical window for optical inspection so as to prevent cross-interference in an automatic inspection apparatus.

3. The plate according to claim 1, wherein the well-forming structure comprises individual filling channels and venting channels for individually filling single wells.

4. The plate according to claim 1, wherein the well-forming structure comprises a chemically stable polymer.

5. The plate according to claim 1, wherein the opening area of the filling opening is larger than the opening area of the venting opening.

6. The plate according to claim 1, wherein the chemically stable polymer is a polypropylene that is optically clear or opaque such that it can be used for fluorescent analysis of a reagent.

7. The plate according to claim 1, wherein the filling opening and the venting opening of a well are located in a filling area which is located aside the horizontal cross section of the well, wherein the filling area corresponds to the area neighbored to the well according to the pitch of the plate, so that the filling areas and the horizontal cross sections of the wells of at least one of the columns and the rows of wells of the plate are arranged in alternating sequences.

8. The plate according to claim 1, wherein the well-forming structure is placed on top of the bottom layer so that the bottom layer provides the bottom of the wells.

9. The plate according to claim 1, wherein at least one of the cover and the bottom layer is a foil.

10. The plate according to claim 1, wherein at least one of the cover and the bottom layer comprises at least two layers.

11. The plate according to claim 10, wherein the bottom layer comprises an upper layer made of a plastics material directed to the liquid sample and a lower layer made of a metal directed to the thermal cycling means.

12. The plate according to claim 1, wherein at least one of the cover and the bottom layer is a composite foil.

13. The plate according to claim 1, wherein the bottom layer has a thermal conductivity of at least 20 $Wm^{-1}K^{-1}$.

14. The plate according to claim 1, wherein the bottom layer has a thermal conductivity of at least 200 $Wm^{-1}K^{-1}$.

15. The plate according to claim 1, wherein the well-forming structure comprises a well-covering area in between and connecting webs that project above and below the well-covering area for providing the thermal insulating air distance between the well-covering area of the well-forming structure and the cover placed on top of the webs and which is fixed to the webs.

16. The plate according to claim 1, further comprising a sample distribution structure comprising a filling opening and a common filling channel common to numerous wells for filling numerous wells with a liquid sample via the filling opening.

17. A high-density multiwell-plate for performing thermocycled amplification reactions of polynucleotides in liquid samples, said plate comprising:

- a plurality of reaction wells for thermal processing and nucleic acid amplification of the liquid samples and said plate being designed to be thermally processed by a thermal cycling means of an apparatus for analyzing the liquid samples;
- a substantially planar bottom layer for providing a thermal contact of the plate to a thermal cycling means;
- a rigid well-forming structure placed above the bottom layer defining single wells, wherein the well-forming structure comprises rigid substantially horizontal well-covering areas that cover the liquid sample comprised in the wells at the top side of the liquid sample;
- a substantially planar cover placed above or on the top side of the well-forming structure, wherein the cover provides a sealing cover of the wells and a thermal insulating air distance between the well-covering areas of the well-forming structure and the cover; and
- at least a first filling and venting structure and a second filling and venting structure configured to be coupled to the substantially planar bottom layer and the substantially planar cover and configured so that the first filling and venting structure and the second filling and venting structure are located on opposite sides of the rigid well-forming structure, forming a filling channel comprising a filling opening and a venting channel comprising a venting opening and configured such that a liquid sample placed in the filling opening flows into the filling channel and under the rigid well-forming structure to fill the well; and
- wherein an opening area of each of the filling openings is larger than an opening area of each of the venting openings.

18. The plate according to claim 17, wherein the filling opening and the venting opening of a well are located in a filling area which is located aside the horizontal cross section of the well, wherein the filling area corresponds to the area neighbored to the well according to the pitch of the plate, so that the filling areas and the horizontal cross sections of the wells of at least one of the columns and the rows of wells of the plate are arranged in alternating sequences.

19. A high-density multiwell-plate for performing thermocycled amplification reactions of polynucleotides in liquid samples, said plate comprising:

- a plurality of reaction wells for thermal processing and nucleic acid amplification of the liquid samples and said plate being designed to be thermally processed by a thermal cycling means of an apparatus for analyzing the liquid samples;
- a substantially planar bottom layer for providing a thermal contact of the plate to a thermal cycling means;
- a rigid well-forming structure placed above the bottom layer defining single wells, wherein the well-forming structure comprises rigid substantially horizontal well-covering areas that cover the liquid sample comprised in the wells at the top side of the liquid sample;
- a substantially planar cover placed above or on the top side of the well-forming structure, wherein the cover provides a sealing cover of the wells and a thermal insulating air distance between the well-covering areas of the well-forming structure and the cover;
- at least a first filling and venting structure and a second filling and venting structure configured to be coupled to the substantially planar bottom layer and the substantially planar cover and configured so that the first filling and venting structure and the second filling and venting structure are located on opposite sides of the rigid well-forming structure, forming a filling channel comprising a filling opening and a venting channel comprising a venting opening configured such that a liquid sample placed in the filling opening flows into the filling channel and under the rigid well-forming structure to fill the well; and
- wherein the filling opening and the venting opening are located in a filling area which is located aside the horizontal cross section of the well, wherein the filling area corresponds to an area neighbored to the well according to the pitch of the plate, so that the filling areas and the horizontal cross sections of the wells of at least one of the columns and the rows of wells of the plate are arranged in alternating sequences.

20. The plate according to claim 19, wherein the well-forming structure is placed on top of the bottom layer so that the bottom layer provides the bottom of the wells, and the well-forming structure comprises a well-covering area in between and connecting webs that project above and below the well-covering area for providing the thermal insulating air distance between the well-covering area of the well-forming structure and the cover, wherein the cover is placed on top of the webs and which is fixed to the webs.

* * * * *